United States Patent
Giusfredi et al.

(10) Patent No.: US 10,101,208 B2
(45) Date of Patent: Oct. 16, 2018

(54) APPARATUS AND METHOD FOR MEASURING THE CONCENTRATION OF TRACE GASES BY SCAR SPECTROSCOPY

(71) Applicant: CONSIGLIO NAZIONALE DELLE RICERCHE, Rome (IT)

(72) Inventors: Giovanni Giusfredi, Sesto Fiorentino (FI) (IT); Iacopo Galli, Sesto Fiorentino (FI) (IT); Pablo Cancio Pastor, Sesto Fiorentino (FI) (IT); Davide Mazzotti, Sesto Fiorentino (FI) (IT); Paolo De Natale, Firenze (FI) (IT)

(73) Assignee: CONSIGLIO NAZIONALE DELLE RICERCHE, Rome (IT)

( * ) Notice: Subject to any disclaimer, the term of this patent is extended or adjusted under 35 U.S.C. 154(b) by 52 days.

(21) Appl. No.: 14/784,705

(22) PCT Filed: Apr. 15, 2014

(86) PCT No.: PCT/IB2014/060739
§ 371 (c)(1),
(2) Date: Oct. 15, 2015

(87) PCT Pub. No.: WO2014/170828
PCT Pub. Date: Oct. 23, 2014

(65) Prior Publication Data
US 2016/0054180 A1    Feb. 25, 2016

(30) Foreign Application Priority Data
Apr. 15, 2013    (IT) .............................. PD2013A0095

(51) Int. Cl.
*G01J 3/42*    (2006.01)
*G01N 21/35*    (2014.01)
(Continued)

(52) U.S. Cl.
CPC .............. *G01J 3/42* (2013.01); *G01J 3/0205* (2013.01); *G01N 21/274* (2013.01);
(Continued)

(58) Field of Classification Search
CPC ........................................................ G01J 3/42
See application file for complete search history.

(56) References Cited

U.S. PATENT DOCUMENTS 8,654,334 B1 *   2/2014  Gupta .................... G01N 21/33
                                                                356/437
2004/0065816 A1 *  4/2004  Ye ............................. G01J 3/42
                                                               250/227.18
(Continued)

FOREIGN PATENT DOCUMENTS

DE        202009011701 U1    2/2011

OTHER PUBLICATIONS

I. Galli et al. "Molecular Gas Sensing Below Parts Per Trillion: Radiocarbon-Dioxide Optical Detection" Physical Review Letters, vol. 107, No. 27 Dec. 1, 2011, XP055072432, pp. 270802(1)-270802(4).
(Continued)

*Primary Examiner* — David Porta
*Assistant Examiner* — Jeremy S Valentiner
(74) *Attorney, Agent, or Firm* — Volpe and Koenig, P.C.

(57) ABSTRACT

The present invention relates to a ring-down spectrometry apparatus in absorption saturation condition, for measuring the concentration of a gas through a measurement of the spectrum of a molecular transition of said gas. The apparatus includes a laser source, an adjuster for varying the wavelength of said radiation emitted by said laser, and a resonant cavity. A photodetector is adapted to detect an electromagnetic radiation beam and is adapted to generate a decay signal. An electronic circuit receives the signal from the photodetector and is adapted to convert it to a processor. A
(Continued)

processor is adapted to receive said decay signal from the photodetector and perform interpolation to obtain a concentration of said gas.

11 Claims, 8 Drawing Sheets

(51) Int. Cl.
G01N 21/3504 (2014.01)
G01N 21/39 (2006.01)
G01J 3/02 (2006.01)
G01N 21/27 (2006.01)
G01N 21/03 (2006.01)

(52) U.S. Cl.
CPC ......... *G01N 21/3504* (2013.01); *G01N 21/39* (2013.01); *G01N 21/031* (2013.01); *G01N 2201/068* (2013.01); *G01N 2201/06113* (2013.01)

(56) References Cited

U.S. PATENT DOCUMENTS

2007/0147585 A1   6/2007   Eilbert et al.
2013/0027696 A1*  1/2013   Sekiyama ............... G01J 3/513
                                                 356/300

OTHER PUBLICATIONS

Giusfredi et al. "Saturted-Absorption Cavity Ring-Down Spectroscopy" Physical Review Letters, vol. 104, No. 11, Mar. 19, 2010, pp. 110801(1)-110801(4).

I. Galli et al. "Ti:sapphire laser intracavity difference-frequency generation of 30mW cw radiation around 4:5 μm" Optics Letters, vol. 35, No. 21, Nov. 1, 2010, pp. 3616-3618.

* cited by examiner

APPARATUS AND METHOD FOR MEASURING THE CONCENTRATION OF TRACE GASES BY SCAR SPECTROSCOPY

CROSS REFERENCE TO RELATED APPLICATIONS

This application is a 371 of International Application No. PCT/IB2014/060739 filed Apr. 15, 2014, which claims the benefit of Italian Application No. PD2013A000095, which was filed on Apr. 15, 2013, and are incorporated herein by reference as if fully set forth.

FIELD OF INVENTION

The present invention relates to an apparatus employing an optical detection technique called saturated-absorption cavity ring-down spectroscopy (which hereafter will be referred to as SCAR for brevity) for detecting the concentration of trace gases, in particular for trace gases present in part per trillion ($10^{-12}$), for example for the detection of radiocarbon at concentration levels much lower than those present as natural abundance.

BACKGROUND

The so-called method of $^{14}C$ (carbon-14 or radiocarbon), is a radiometric dating method based on the measurement of relative abundances of carbon isotopes. The method of $^{14}C$ allows dating organic materials (bone, wood, textile fibers, seeds, wood, coals . . . ), thus containing carbon atoms.

Carbon is a chemical element essential to life and present in all organic substances. It is present on earth in three isotopes: two stable ones ($^{12}C$ and $^{13}C$) and a radioactive one ($^{14}C$). The latter turns by beta decay into nitrogen (N—$^{14}$), with an average half-life of 5730 years, thus this isotope would disappear in the long run, if not continually reinstated. The production of new $^{14}C$ regularly occurs in nature in the high layers of the troposphere and in the stratosphere, by the capture of thermal neutrons, secondary components of cosmic rays, by the nitrogen atoms present in the atmosphere. The dynamic balance between production and radioactive decay then keeps the concentration of $^{14}C$ in the atmosphere constant, where it is mainly bound to oxygen in the form of carbon dioxide.

All living organisms that are part of the carbon cycle are continuously exchanging carbon with the atmosphere through breathing (animals) or photosynthesis (plants) processes or they assimilate it by feeding on other living beings or organic substances. Consequently, until a body is alive, the isotopic ratio of $^{14}C$ and that of the other two carbon isotopes remains constant and equal to what is found in the atmosphere. In particular, the current natural isotopic ratio (abundance) in the atmosphere is:

$$r_0 = \frac{^{14}C}{C} \approx 1.2 \times 10^{-12}.$$

After death, these processes end and the organism does not exchange carbon with the outside anymore. Then, as a result of decay, the isotopic ratio decreases on a regular basis according to the formula: $r=r_0 e^{-\Delta t/\tau}$, where $\Delta t$ is the time elapsed from the death of the organism and $\tau$ is the average lifespan of $^{14}C$.

By measuring the amount of $^{14}C$ present in organic remains, the age thereof is obtained by applying the following formula: $\Delta t=-\tau \ln(c/c_0)$.

The measurement of $^{14}C$ is possible, given the low concentrations present, with the method of mass spectrometry (AMS, Accelerator Mass Spectrometry): using a mass spectrometer, the concentration of $^{14}C$ present in the sample is measured. This method is able to obtain reliable measurements for concentrations in the order of $$\frac{^{14}C}{C} \approx 10^{-15}.$$

However, the costs related to AMS equipment are relevant, in the order of millions of euros, and the overall dimensions of the same equipment is substantial, with high operating voltages.

Additionally, the detection of trace gases is generally very relevant in various technology fields. Apart from dating, the measurement of the amount of radiocarbon is important in biomedicine or in environmental and earth science.

The conventional cavity ring-down (CRD) spectroscopic technique was devised over 20 years ago, using pulsed laser first and then continuous emission laser. The advantages of CRD are mainly two, as detailed below: the signal is immune to width fluctuations of the radiation source used, and the linear absorption coefficient is measured directly and then, knowing the total pressure of the gas and the line-strength of the spectroscopic transition, the concentration of the molecular species to be measured.

A class of techniques for measuring the concentration of a gas is spectroscopy. Spectroscopy is a scientific technique that analyzes the spectrum of electromagnetic radiation emitted by a source split in its wavelengths and hence it analyze the properties of atoms or molecules that are the source of such radiation. In these spectra, the lines of absorption or emission can be studied.

The origin of a given spectral line can be an electronic, vibrational or rotational transition of the molecule of interest. For example, in the infrared, the main origins of a spectral line are not transitions between energy levels of electrons, generally dominating in the visible spectrum, but transitions between molecular vibrational energy levels.

A typical CRDS spectroscopy includes an apparatus comprising a laser that is used to send a highly fine coherent radiation beam consisting for example of two highly reflective mirrors (for example with a R>99.9%). When the radiation emitted by the laser is in resonance with a cavity mode, the radiation intensity increases in the cavity due to constructive interference phenomena. The laser is then quickly switched off, or moved away from the resonance cavity, in order to measure the exponentially decreasing intensity of light that escapes from the cavity. During this decay, the light is reflected back and forth thousands of times by the mirrors giving an effective path along a few miles.

If a gas or a mixture of gases that absorb light is placed inside the cavity, the intensity of photons trapped decreases by a fixed percentage along each path inside the cavity due to the scattering and absorption by the medium in the cavity and due to reflectivity losses. The light intensity inside the cavity is then given by an exponential function of time: $I(t)=I_0 \exp(-t/\tau)$.

CRD spectroscopy measures how long $\tau$ (time) light employs for its intensity to decay to 1/e of its initial intensity value, and this value of ring-down time is used to calculate the concentration of the absorbing substance in the gas inside the cavity.

The operating principle is thus based on the extent of a decay rate rather than an absolute absorbance. The decay constant τ is called "ring-down" and is dependent on loss mechanisms inside the cavity. For an empty cavity, i.e. without an absorbing medium inside, the decay constant $\tau_0$ is dependent on mirror losses (transmission, absorption and scattering) and various optical phenomena such as diffraction:

$$\tau_0 = \frac{n}{c} \cdot \frac{l}{1 - R + X},$$

where n is the refractive index of the medium in the cavity, c the speed of light in vacuum, l is the length of the cavity, R the reflectivity of the mirrors, and X takes into account various other optical losses. The equation uses the $\ln(1+y) \approx y$ approximation for y close to zero, which is the case in the working conditions of the CRD.

A gas inside the cavity absorbs energy by increasing the losses according to the Beer-Lambert law and then the intensity decays more quickly. Therefore, assuming that the gas fills the entire cavity, the decay time becomes:

$$\tau = \frac{n}{c} \cdot \frac{l}{1 - R + X + \alpha l},$$

where α is the absorption coefficient of specific gas tested. This is called a linear approximation as α is considered independent of the intensity of the radiation.

In other words, the cavity ring-down event occurs by abruptly stopping the radiation from the laser that impinges on the cavity and is characterized by a power transmitted which decays according to the exponential function $\exp(-\gamma t)$, where $\gamma = 1/\tau$ and t is the time measured from the moment of interruption of the incident wave.

If the cavity has an internal linear absorbing medium, the constant γ is simply the sum of two terms: γc representing the empty cavity contribution and γg which represents that of the medium absorption. With two measures, one with empty cavity and one with absorbent medium, the value of γg can therefore be ideally determined.

Recently, a new technique was presented related to laser spectroscopy, called "saturated-absorption cavity ring-down spectroscopy" (hereinafter briefly SCAR), described in "Saturated-absorption cavity ring-down spectroscopy" written by G. Giusfredi et al., Phys. Rev. Lett. 104, 110801 (2010), which has proven that high sensitivity can be achieved. This technique is called below ring-down spectroscopy under saturation of absorption. This means that the intensity of light radiation in the cavity that is set is much greater than the saturation intensity of the molecular transition to detect.

SCAR spectroscopy uses a non-linear model bringing the absorbing medium to saturation, i.e. the intensity of the laser beam is such as to lead the molecular transition of the gas of interest—resonant with the laser—to saturation. In other words, the wavelength of the electromagnetic radiation emitted by the laser is adjusted so that it is in resonance with the transition of interest and the intensity of the radiation itself is increased or adjusted so that this transition is brought to a saturation condition. From the studies reported by the Applicants, they have figured out how to take advantage of the fact that a cavity containing a gas in high saturation conditions behaves almost as a empty cavity in relation to radiation, i.e. when the laser is switched off, the emission of photons follows a curve similar to that of the empty cavity at least for a first time interval. This scheme is called "effective empty cavity scheme". Therefore, in an experiment where saturation is reached inside the cavity using a beam having a sufficient intensity and then turning off the same, measuring the radiation emitted with a photodetector, a curve is obtained that for a first part follows the decay pattern in an empty cavity. After a certain period of time, however, the behavior of the radiation emitted is no longer that of an empty cavity, since many photons have already left the cavity that contains a gas that is no longer under saturation conditions, thus for a second time interval the decay curve is the curve that one would get if the cavity was filled by a non-saturated gas, i.e., one gets back to the linear scheme. Thus, by measuring the radiation emitted by the cavity, the two decays are measured together, using both the saturation condition and the linear condition, and thus they may be subtracted in order to obtain the decay due solely to the gas in the cavity.

In this way it is possible to obtain both the contribution γc of the empty cavity and that γg of the gas under linear absorption at low intensity from the same decay event. In other words, the value of γg is encoded in the deformation of exponential decay. Since in principle all information to be obtained is contained in the same decay event, the SCAR spectroscopy minimizes the following errors that are introduced in the measures and cause not to be in an ideal condition, essentially preventing two measures as in conventional CDR spectroscopy:

the non-monochrome condition of the wave emitted by the laser which is incident inside the cavity;
the imperfect immediacy of the interruption of the wave to be "turned off" to measure the ring-down time;
the fluctuations of the resonant frequency of the cavity;
the imperfect adaptation of the spatial mode of the incident wave produced by the laser with the cavity mode, which can also vary over time;
the reflectivity unevenness of the mirrors forming the cavity, which combines with the alignment fluctuations of the incident wave;
the dependence of γc on frequency, if to go from "full cavity" to "empty cavity" different longitudinal resonant modes of the cavity are used, one coincident with a region of absorption of the medium (i.e. the gas introduced into the cavity the concentration of which is to be measured) and one in a region of transparency;
the fluctuation of this dependency over time.

To give a quantitative idea of the resolution obtainable through the SCAR technique, consider the special case of radiocarbon dioxide detection in natural abundance. In optimum conditions of temperature and pressure, the deformation from a pure exponential produced by radiocarbon along decay signals is of the order of 1 μV on 3 V. This places very stringent limits on the residual non-linearity which can be borne.

The measurement is possible thanks to the noise present in the signal to be captured, which in good approximation has no or at least constant average. By mediating many events (each decay signal deposited in memory is the average of 1280 events), it is possible to increase the resolution of digitisation by approximately 35 times.

SUMMARY OF THE INVENTION

The invention relates to an apparatus for the measurement of the concentration of a gas on the basis of the SCAR method outlined above, i.e. by measuring the temporal evolution of the ring-down in a condition of saturation of the transition of interest.

As indicated above, the SCAR spectroscopy methodology is based on a fit of a curve of the ring-down signal detected in conditions of resonance between the electromagnetic radiation emitted by the laser and the cavity and between the electromagnetic radiation emitted by the laser and the gas transition that has distortions in relation to a perfect decreasing exponential, exponential which represents the decay curve in linear condition. Just because a saturation condition is used, all the measurement is based on non-linear absorption of trace gas located within a high-finesse cavity containing the gas itself. The exponential is thus distorted. The extent and shape of the distortion contain information on the absorption that the gas would have in linear condition and thus on its concentration.

In particular, to avoid altering the information contained in the exponential distortion, it is therefore necessary to avoid introducing further distortions that would create spurious signals.

An object of the invention is to provide an apparatus that allows minimizing or even eliminating the distortion in the output signal in order to obtain very precise measures. In particular, the invention is intended to minimize systematic errors in the measure, and more particularly to minimize systematic non-linearity present in the measurement carried out as detailed above.

The apparatus of the invention includes a laser source to send a coherent electromagnetic radiation at a fixed wavelength. The laser source emits a radiation with an intensity such as to work under conditions of saturation, as described below. The laser preferably emits infrared radiation. The infrared represents the optimal spectral range since it has the most intense absorption bands of gaseous molecular species to be detected. Preferably, the laser emits radiation at a single wavelength, and more preferably it is a tunable laser (that can be tuned), i.e. whose wavelength is selectable within a certain range. This selection occurs in a known manner by means of modification of the wavelength which are known in the field. As is known, no laser is perfectly monochromatic, the laser of the invention is preferably a laser with a very narrow line width, for example a CW laser wherein the line width is less than the width of a cavity mode.

In addition, the apparatus includes a resonant cavity with high fineness, e.g. comprising two reflecting mirrors arranged in such a way as to form a closed optical path for the electromagnetic radiation emitted by the laser source. Preferably, the distance between the two mirrors is finely adjustable (within a range of a few microns with sub-nm resolution) so as to put the cavity in resonance with the laser radiation, so as to match the electromagnetic radiation to the cavity. The movement of the mirrors occurs through appropriate moving means known in the field. Preferably, the reflectivity of the mirrors of the cavity must be greater than 99.9%.

The resonant cavity is intended to contain the gas of which the concentration is to be detected.

The arrangement of the laser source and of the cavity can be adjusted in such a way that the single wavelength light radiation emitted by the source is coupled with the cavity, so that it is trapped therein, forming a resonant radiation.

If the laser is not monochrome, it is necessary that only one wavelength is substantially coupled inside the cavity.

The type of laser source used in the present invention is for example described in the article written by Galli et al.,
Opt. Lett. 35, 3616 (2010). Other types of laser sources can be used, the intensity of the radiation emitted must however be such that the intensity of radiation I inside the cavity is much greater than the saturation intensity $I_S$ of the molecular transition to be detected, i.e. $I \gg I_s$ where $$I_s = ch\frac{\Gamma_{//}\Gamma_{\perp}k^3}{A},$$

where A is the Einstein transition coefficient, k is the wave vector and $2\pi\Gamma_{//}$, $2\pi\Gamma_{\perp}$ are respectively the decay rate of the population and of the coherence associated with the transition of interest.

Preferably, the saturation parameter, i.e. the ratio between the intensity of the light radiation within the cavity and the intensity of saturation of the molecular transition to be detected, or I/Is, must be >10.

The radiation/cavity combination enables an increase in the intensity of the radiation due to the resonance phenomenon. For a linear cavity, being X the wavelength of the radiation coming from the laser and D the distance between the two mirrors, the cavity must satisfy the equation $$D = \frac{m\lambda}{2}$$

with m integer.

The gas of which the concentration is to be measured is located within the cavity. Therefore, the cavity preferably includes an inlet and an outlet of the gas contained in dedicated containers. The cavity also includes, preferably, means for the thermal adjustment of the cavity itself so as to adjust the gas temperature, and pressure gauges to adjust the gas pressure inside the cavity.

The measures are carried out by bringing the cavity in resonance with the electromagnetic radiation emitted by the laser, injecting it with the laser radiation to beyond a predetermined filling level. This coupling between the radiation and the cavity may be initially performed by the movement of the two mirrors so as to vary the total length of the cavity and reach a cavity-laser resonance condition.

Preferably, as mentioned above, the laser emits radiation at different frequencies (or wavelengths) and light radiation at various frequencies is introduced into the cavity, by scanning in a certain range of frequencies. Such a scan is carried out in a neighborhood of a molecular transition frequency of the gas to be studied and the traces of which are to be detected, in order to measure the spectral area of the molecular transition, which is proportional to the gas concentration.

Furthermore, the apparatus of the invention comprises a detector, in particular a photo detector, adapted to detect the outgoing radiation from the cavity.

The electrical signal from the photodetector is sent to a processor. The processor processes such an input signal by a fit of the signal with a function that takes into account the effects of saturation, to calculate the decay time and thus the gas concentration present within the resonant cavity.

The detection is performed as follows: after the radiation has been introduced inside the cavity and a saturation condition has been obtained (i.e. in which the intensity of the radiation is much greater than the intensity of saturation of the molecular transition of interest), the coupling between the cavity and the radiation emitted by the laser source is interrupted by any means known in the art and the time decay of the radiation within the cavity itself is measured. For example, the coupling between the cavity and the laser source can be interrupted by switching off the laser source and/or by rapidly changing the emission frequency.

In order to take a ring-down measurement, the laser and the cavity are brought into a resonance condition, i.e. a condition in which the wavelength of the laser is a multiple of the optical path in the cavity. Therefore, all the measures described below, both those of calibration and the actual ones to measure the gas concentration, are carried out in a condition in which initially there is resonance between the electromagnetic radiation emitted by the laser and the resonant cavity. This resonance, hereinafter briefly called cavity-laser resonance, is "switched off" to perform the actual ring-down measurement.

Furthermore, to perform a measurement of the gas concentration, a further resonance condition is imposed which is the resonance condition between the electromagnetic radiation emitted by the laser and the molecular transition of interest. This resonance condition is not always present, it is not for example in calibration measurements, as detailed below. This additional resonance will be briefly called laser-gas resonance hereinafter.

With an apparatus for SCAR spectroscopy, as already noted above by the same Applicants, some problems present in the conventional CRD spectroscopy are solved. However, there are additional sources of noise that can cause a non-detection capability of very low gas concentrations when the above measurement is made.

Among the leading causes of error we may identify:
the non-uniformity of the photodetector, which is coupled with the fluctuations in the shape and position of the transmitted wave;
the non-linearity in the photodetector response;
the non-linearity of the amplification and digitization electronics.

In addition, shape fluctuations of the beam in output from the cavity contribute to this noise which affect the detector and which are coupled to its inherent non-uniformity. These fluctuations in turn result from the way in which the cavity was injected, for its vibrations and those of the incident beam.

Although the profile of the transmitted beam observed appears to be stable, it must be assumed that it is not at the levels necessary for the measurement. In fact, both the injection and of course the decay are transient events, far from the stationary conditions of the ideal case mentioned at the beginning. A non-perfect alignment of the incident beam, combined with the laser-cavity resonance conditions, breaks the axial symmetry of the field in the cavity. The detuning of the cavity in fact affects both the field shape during its injection and on the other hand the cavity has a small oscillation in length to search for resonance. After the switching off, when the transmitted power reaches a threshold value, the field shape in the cavity continues to evolve, and this affects the wave transmitted. Most of these fluctuations are random and can be averaged away.

Therefore, this source of error can be minimized, for example by averaging over many ring-down events that are measured by the apparatus of the invention.

However, there remain systematic effects that essentially depend on the mutual alignment between the various parts of the detection system, i.e. source-cavity-photodetector that, even without altering the system manually, have fluctuations over hours. These effects result in a reduced repeatability of the line profile area for the measurement of which a few hours are required with the averaging procedure mentioned above.

A consequence of these variations in the beam shape is clear observing the residues of a fit with an exponential curve of the decay signals obtained with an apparatus according to the prior art. Coupled with the unevenness of the detector surface, these fluctuations give residues that oscillate along the time axis with an amplitude of up to a few tens of mV with 3V signal. The same measurements were repeated using different photodetectors and fluctuations were observed in all cases, even using the best detector among the three tested.

According to the invention, both a hardware device and a software device were set up to reduce as much as possible the systematic effect due to mutual alignment between the various parts of the detection system, i.e. the source-cavity-photodetector that, even without altering the system manually, has fluctuations over hours. These systematic effects are non-linear.

Additionally, as mentioned above, according to the prior art, even the best commercially available photodetectors do not have a perfectly linear response with the power of the incident radiation.

There is some non-linearity in the signal detected that is introduced by the same photodetector, non-linearity that is important in case of measurements of trace gases with concentrations equal to one part of $10^{12}$.

In particular, according to the invention, in the apparatus, a diffuser element is interposed between the photodetector and the cavity which is adapted to spread the radiation before it reaches the photodetector itself. Preferably, the apparatus also includes means for focusing the light radiation outgoing from the cavity and even more preferably, such a diffuser element is arranged downstream, with reference to the path of the light signal, of the focusing means, so as to be interposed between the focusing means and the photodetector.

The presence of the diffuser allows increasing the accuracy of the signal obtained.

The diffuser element at least partly evens the signal that reaches the surface of the photodetector, for example preventing the signal from mainly reaching some points of the same, and at the same time reduces the length of spatial correlation of the beam on the illuminated surface of the photodetector, randomly varying the interference fringes that may form on the surface of the same, on a length scale shorter than that of the spatial heterogeneity of its response.

In this way, even if the alignment between cavity-focusing means and photodetector fluctuates, the effect on the photodetector is made "even".

Additionally, the diffuser element decreases the power of the signal that is focused on the photodetector itself: the intensity that must be used by the laser beam is high in order to achieve saturation of the gas in the cavity, however such a power can be detrimental in case a signal of this type reaches the detector itself.

The diffuser element ensures illumination on the photodetector as uniform as possible and independent of the spatial fluctuations of the beam transmitted by the cavity.

Preferably, the diffuser element is a surface diffuser element. In a different preferred example, the diffuser element is volumetric.

In one version, the diffuser element comprises a volumetric diffuser element combined with a surface diffuser element.

The apparatus of the invention is further provided with a processor that receives the signal from the photodetector and that, through a suitable algorithm, modifies the signal received to eliminate the further systematic non-linearity mentioned above. The software-diffuser element combination minimizes the non-linearity due to the source-cavity photodetector alignment which is variable over time.

This signal received of which the parameters are to be measured so as to obtain the gas concentration is revealed in resonance conditions, i.e. in resonance conditions between the electromagnetic radiation emitted by the laser and the molecular transition of the gas of interest. Obviously, being a ring-down measure, a resonance condition also exists between the electromagnetic radiation emitted by the laser and the cavity. The signal in resonance conditions between the electromagnetic radiation emitted by the laser and the transition of the gas is called "laser-gas resonance signal" hereinafter, according to the nomenclature used above.

The processor of the invention performs an interpolation of the received signal in terms of laser-gas resonance so as to obtain a concentration of the gas to be measured as interpolation parameter, but before this, it is "modified" or corrected by parameters that are measured through the acquisition of a decay signal in laser-gas non-resonance, i.e. in which the electromagnetic radiation emitted by the laser is not in a condition of resonance with the gas. Both signals detected in laser-gas resonance or in laser-gas non-resonance are laser-cavity resonance signals.

In order to perform the above interpolation, it is assumed that in the absence of gas to be measured within the cavity, the decay profile is a pure exponential as already seen, with amplitude A and bottom F:

$$y(t)=Ae^{-\gamma_c t}+F \qquad (1)$$

and what deforms it is a systematic perturbation d, attributed to a first approximation only to the effects of non-linearity of the detection, amplification and digitization of the electronics used and connected to the photodetector, i.e. the non-linear systematic errors that according to the invention are to be minimized. The signal acquired S(t) via the photodetector and managed by the processor is therefore given by $$S(t)=y(t)+d(S(t)). \qquad (2)$$

Once perturbation d has been acquired as a function of signal S, it is possible to reconstruct the "true" signal y(t) as:

$$y(t)=S(t)-d(S(t)). \qquad (3)$$

The procedure to calibrate and then subtract this disturbance d, which can be considered small compared to the dynamic range of signal S, is as follows.

a) At the beginning of a measurement cycle, with the laser out of resonance with the species to be measured, various decay signals are acquired in laser-gas non-resonance condition (but in laser-cavity resonance condition) using the same or similar procedure of acquisition of the measures of the line profile of the spectrum in laser-gas resonance as described above, as much as possible in the same identical experimental conditions.

b) A fit of these decays is performed using equation (2) where perturbation d is given for example by a Fourier series truncated to 12 terms, periodical on an appropriate range close to the dynamic range of the acquired signals. Since d is relatively small, eq. (2) is implemented iteratively, preferably in at least two steps in the fit function:

$$s(t)=y(t)+d(y(t)),$$

$$s'(t)=y(t)+d(s(t)), \qquad (4)$$

where s, s', . . . , are successive approximations of S.

c) The value of S(t) is compared with the measured data and the parameters of function d, together with those of y, are determined by standard fit methods, such as with the ordinary method of chi-square minimization.

d) The parameters of function d are stored for use in subsequent measurements of the line profile.

e) Finally, for the acquisition of the line profiles, eq. (3) is applied to the data of the single decay events that reach the acquisition instrument, recovering the "true" signal for subsequent analysis by the SCAR method of variable separation $\gamma c$ and $\gamma g$.

The procedure for the acquisition of line profiles, i.e. spectroscopy, contains an option whereby one can choose whether or not to apply the correction of equation (3) to the data, so it can be used in step a) disabling the correction and then enabling it again in the measurements of the profiles in step e).

The need to repeat the calibration at each series of profile measurements, typically every hour of measurement, results from the fact that the perturbation does not actually depend only on the electronics of the detection, but also on the optical-mechanical problems mentioned above.

Therefore, according to the invention, the apparatus works as follows: an electromagnetic radiation beam at a predetermined wavelength is sent by the laser source inside the cavity where the beam is reflected, for example between the two reflecting mirrors of the cavity, so as to enter in laser-cavity resonance. The mirrors are as much as possible reflective so as to minimize optical losses of the cavity. The distance between the two mirrors is preferably adjusted so as to obtain the laser-cavity resonance mentioned. Once the gas saturation condition has been reached, the radiation is decoupled from the cavity in one of the ways indicated above, and the decay of the radiation present in the cavity is measured, revealing the power of the outgoing radiation from the cavity itself through the photodetector.

Preferably, this measurement is made for every single complete ring-down event of temporal duration as explained above. The measurement is carried out in a condition in which the electromagnetic radiation is in resonance with respect to the gas transition (or to the absorption line of the gas).

The signal in laser-gas resonance in output from the photodetector is sent to the processor that performs an interpolation: the curve obtained for the decay of intensity over time is interpolated using a suitable fit curve, as indicated above. One of the fit parameters thus made is the gas concentration in the cavity.

In addition, the method includes a further measurement and a different interpolation in a different condition. The further measurement is carried out before the measurement outlined above, bringing the radiation out of resonance with respect to the gas absorption (i.e. in laser-gas non-resonance but still in laser-cavity resonance), but at the same time keeping all other experimental conditions unchanged. In particular, a measurement of the decay of the power transmitted from the cavity is carried out using the apparatus of the invention. Since in this ideal case it can assumed that the power decay is a perfect exponential, the discrepancies between such an "ideal" curve, i.e. the calculated one, and that measured can be observed. The differences found are used to correct the curves measured in non-linear condition in laser-gas resonance, in case of saturation as identified above.

The final measurement can for example be an average of 128 ring-down events and on each of these averages it makes the fit and the data analysis. This procedure is preferable to speed up the fit time, but in principle individual events may be analyzed as well.

Therefore, the apparatus of the invention allows minimizing or even eliminating the distortion in the output signal allowing very precise measurements.

DETAILED DESCRIPTION OF THE PREFERRED EMBODIMENTS

Figure 1:
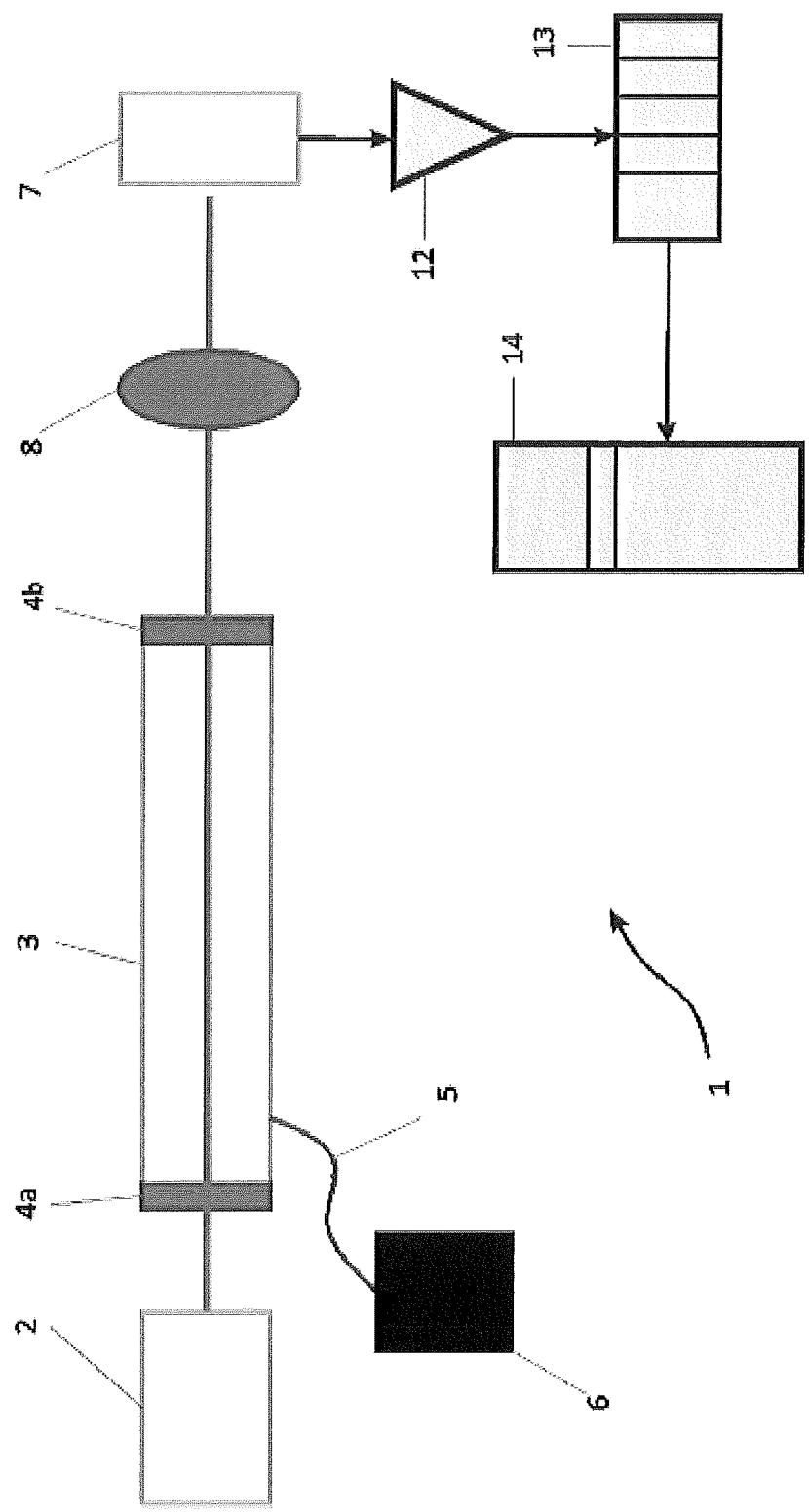
FIG. 1 shows an exemplary diagram of an apparatus made according to the present invention.

With initial reference to FIG. 1, reference numeral 1 indicates an apparatus for SCAR spectroscopy including a laser source 2, for example a continuous wave (CW) coherent laser source generated by a frequency difference tunable over a predetermined range.

Preferably, the radiation emitted by laser source 2 has a wavelength in the mid-infrared, however other wavelengths may be used. The mid-infrared has the advantage of having the strongest molecular absorption.

The type of laser source 2 used in the present invention is for example described in the article written by Galli et al., Opt. Lett. 35, 3616 (2010). Other types of laser sources may be used, provided that the intensity of radiation I inside the cavity is much greater than the intensity of saturation $I_s$ of the molecular transition to be detected, i.e. $I \gg I_s$.

For example, in a range of wavelengths of 4-5 μm, for the transitions of $CO_2$, which have an Einstein coefficient A of about 200 s$^{-1}$, at a pressure of about 12 mbar, Voigt enlargement condition, the power emitted by the laser must be greater than 20 mW, preferably greater than 100 mW.

Apparatus 1 further includes a resonant cavity 3, for example, a cavity having a length of 1 m, provided at opposite ends thereof with two reflecting mirrors 4a and 4b. Preferably, the reflectivity of the mirrors is greater than 99.9%, even more preferably it is greater than 99.99%.

The gas of which the concentration has to be measured is introduced into cavity 3, for example through a duct 5 which connects cavity 3 to a suitable container, such as a cylinder 6.

Apparatus 1 further includes a photodetector 7 suitably arranged for detecting the radiation beam outgoing from cavity 3 as well as a diffuser element 8 interposed between cavity 3 and photodetector 7. The diffuser element 8 is adapted to diffuse the laser beam exiting cavity 3 before it impinges on photodetector 7.

In the apparatus 1 of the invention it is possible to use a surface and/or volume diffuser element.

Figure 2:
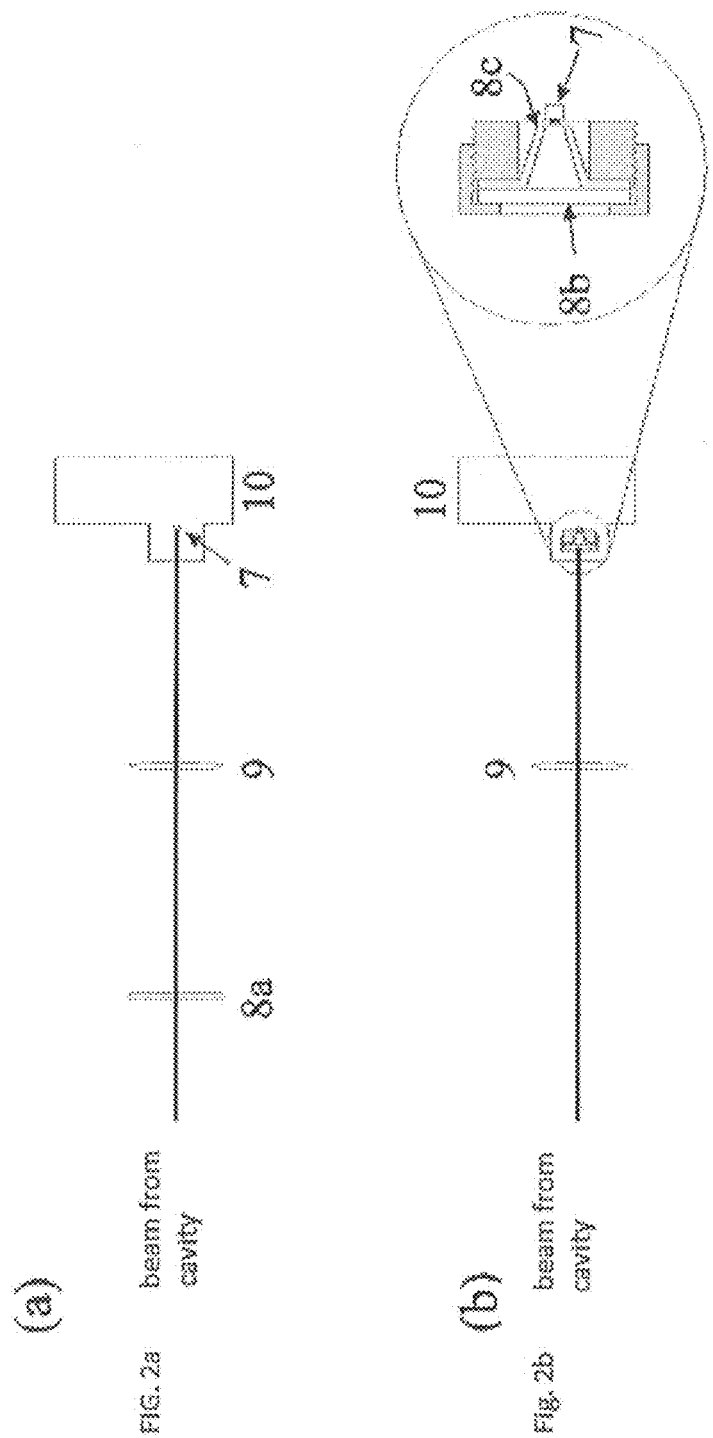
FIG. 2a is a detailed diagram of a first configuration of a diffuser element used in the apparatus in FIG. 1.
FIG. 2b is a detailed diagram of a second configuration of a diffuser element used in the apparatus in FIG. 1.

In the version shown in FIG. 2a, the diffuser element comprises a surface transmission diffuser element 8a, preferably positioned between photodetector 7 and the surface transmission diffuser element 8a there is a lens 9 for gathering the radiation scattered and send it to photodetector 7.

The surface transmission diffuser element 8a is a diffuser slide that has been obtained by grinding the two sides of a microscope slide (25.4×39.3×0.9 mm) with emery consisting of powder of $(Fe, Mg)_3Al_2(SiO_4)_3$ with an average diameter of 23 μm. The grinding was done manually trying to make the opacity of the two sides as homogeneous as possible.

The degree of diffusion obtained with the surface diffuser element 8a is such that looking at the diffused radiation with a camera at 30 cm from the diffuser, the intensity is halved at an angle of approximately 0.1 rad. The geometrical configuration used for SCAR is: resonant cavity 3, diffuser slide positioned at about 35 cm from the output mirror 4b of cavity 3, lens 9 (f=100 mm) positioned at approximately 10 cm from the diffuser slide and photodetector 7 positioned at approximately 10 cm from the focusing lens 9.

A photovoltaic detector InSb (Hamamatsu Photonics, mod. P5968-060) having a circular sensitive area with a 0.6 mm diameter is used as photodetector 7.

Photodetector 7 is cooled in a liquid nitrogen dewar 10, however other suitable cooling elements may be used. Photodetector 7 is cooled in order to minimize the noise due to the thermal black-body radiation background, which at these wavelengths limits the S/N ratio that can be reached.

An overall attenuation factor of the radiation due to absorption and diffusion of approximately 40 is obtained with this configuration.

In this way, the light spot that is formed on photodetector 7 is much larger than the size of the sensitive area of photodetector 7 itself.

On the other hand, the lighting on photodetector 7 is not uniform because of the speckles, or the dotted figures that are obtained when a coherent wave is passed through a disordered medium, generated by the diffuser. Knowing that the spot of the incident beam on the slide has a radius of 1.8 mm, it is possible to calculate the number of speckles on the surface of the photodetector. The number calculated is about 30 speckles having a size of about 100 m in diameter, the number of speckles is therefore high enough to reduce by approximately one order of magnitude the distortion measured as it appears by comparing trace (a) in FIG. 7a with trace (b) in FIG. 7b.

In an alternative version of apparatus 1 of the invention shown in FIG. 2b, a volume transmission diffuser 8b is used.

The advantage of volume diffusers over surface ones is the elimination of the narrow cone of light transmitted but not diffused. A possible volume diffuser is based on a mixture of two powders of different optical materials, and therefore at a different refractive index, both transparent in the mid-IR. The powders will have average diameters larger than the wavelength. Using the different melting temperatures of the two materials of the powders, it is possible to create a conglomerate in which one of the two materials acts as a "cement" and the other as "inclusion". In this way, the light passes through the diffuser undergoing multiple refractions, with angular deviations and random optical paths, at each cement-inclusion interface encountered. Materials with physical (optical and thermal) characteristics suitable to build a good light diffuser at 4.5 μm of the type just described are, for example, cesium iodide (CsI) as cement and calcium fluoride ($CaF_2$) as inclusion.

The features of these materials are shown in the following table:

|  | "Cement" | "Inclusion" |
| --- | --- | --- |
| Structural Code | CsI | $CaF_2$ |
| Refraction index n | 1.74 | 1.40 |
| Thermal expansion α (ppm $K^{-1}$) | 50 | 20 |
| Melting temperature T (K) | 900 | 1670 |

Both materials have the advantage of being transparent also in the visible. In this example, they were chosen to meet some important requirements: $\Delta n=0.34$ is an index jump sufficient to obtain a Lambertian diffusion and a randomization of the light phase capable of minimizing the size of the speckles; $\Delta\alpha=30$ ppm $K^{-1}$, is small enough to avoid thermal stress; $\Delta T=770$ K is a thermal jump more than sufficient to melt the "cement" (e.g. in a furnace) without melting the "inclusion".

If the thickness of the volume diffuser 8b is sufficiently high, in output from the volume diffuser 8b there is a Lambertian distribution of the radiation, with maximum reduction of the size of the speckles. A part of the radiation could also be back-diffused, but that would be at most 50% of that incident, which would in any case be an acceptable loss. The volume diffuser 8b, with a diameter of several mm, as the IR radiation beam, is positioned a few mm from photodetector 7, in this case approximately 4 mm from the photodetector, the effective actual distance between the volume diffuser 8b and the photodetector depending on the type of photodetector used.

Preferably, a surface reflection diffuser 8c is also used together with the volume diffuser 8b, having a conical shape and located downstream with respect to the volume diffuser 8b, so as to be interposed between the volume diffuser 8b and photodetector 7.

The surface reflection diffuser 8c allows sending radiation to photodetector 7 having incidence angles much greater than the radiation that comes directly from the volume diffuser 8b, part of the radiation that would otherwise be dispersed over a large solid angle. In this way, the size of the speckles is further reduced, up to increase their number on the photodetector by more than 2 orders of magnitude compared to the configuration in FIG. 2a, and thus considerably reduce the distortion measured.

The non-linearity of the detector-preamplifier complex is substantially composed of three effects.

A. The laser beam during the transient of each CRD may vary in shape and position on the detector. Since the detector has a local response (responsiveness measured in A/W) that is not uniform on its sensitive surface, these spatial fluctuations of the beam producing a distortion of the detected signal.

B. The detector has a global response that is non-linear, i.e. its responsiveness depends on how much radiation power reaches them. In fact, beyond a certain power level (over 1 mW) it saturates.

C. The conversion electronics of the photocurrent generated by the detector into numbers that can be acquired by processor 14 (transimpedance preamplifier 12 and 18 bit digitizer 13) has a residual non-linearity.

The surface and volumetric diffuser element 8 reduces type A non-linearity since it evenly illuminates photodetector 7, as it forms a large spot on photodetector 7.

However, the diffuser element 8 is unable to compensate for the effects of type B, or type C non-linearity. These two types of non-linearity are compensated, according to the invention, via software using a processor 14 that receives the detection signal from photodetector 7 and that the changes it by using an algorithm developed in accordance with the flow diagram in FIG. 6, as described below.

In the preferred embodiment of the invention, in which the concentration of carbon-14 is to be detected, such a concentration is searched for in the $^{14}C^{16}O_2$ molecules. The target transition is the roto-vibrational transition ($00^01-00^00$) P(20) of the molecule of $^{14}C^{16}O_2$ around 4.5 μm. Therefore, cavity 3 is filled with $CO_2$.

The measurements are carried out by bringing the intensity of the radiation in cavity 3 to high levels of saturation for the gas transition, and then removing the laser beam from the coupling with cavity 3. This coupling may be initially performed by the movement of the two mirrors 4a and 4b so as to vary the total length of the cavity and reach a cavity-laser resonance condition. From this instant, the photons exiting from cavity 3 are detected by photodetector 7, which produces an electrical signal of the decay of the power of the outgoing radiation from cavity 3.

The response time of photodetector 7, such as a photodiode, must be much faster than the decay time of the empty cavity. Several spectroscopic measurements are carried out using a frequency scanning and preferably at each frequency scan there is a dither of the cavity around the laser-cavity resonance condition.

All measurement results are processed by a processor 14 in which there are several algorithms so as to perform appropriate interpolations as described below.

Figure 3:
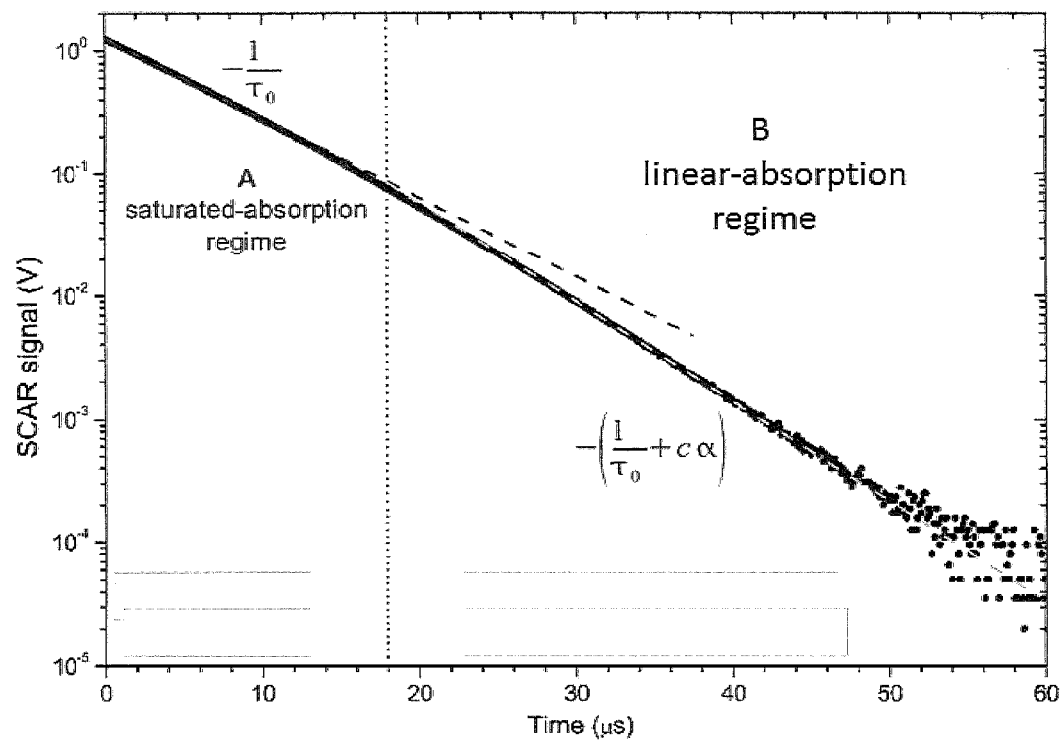
FIG. 3 is a graph of a SCAR signal over time.

The Applicants have already shown that—see Giusfredi G. et al. Phys. Rev. Lett. 104, 110801 (2010)—in conditions of saturation, a signal under these conditions revealed by photodetector 7 is similar to that shown in FIG. 3.

In particular, if we start from saturation conditions and measure the decay of the intensity of the outgoing signal—preferably in each ring-down event—the signal thus obtained by photodetector 7 has a pattern substantially divided into two parts: in a first interval it has an exponential pattern with a certain slope (the graph is made in logarithmic scale) linked to the load losses of cavity 3, while in the the second part the slope of the straight line increases and the increase depends on the gas concentration in cavity 3.

It was assumed that the gas interacts with the radiation in cavity 3 in a $TEM_{00}$ mode with an intensity and power that depend on time in the following way:

$$I(\rho, t) = I_0(t)e^{-2(\rho/w)^2}, \quad (5)$$

$$P(t) = \frac{\pi w^2}{2}I_0(t)$$

where $\rho=\sqrt{x^2+y^2}$ is the radial coordinate and $I_0(t)=(\rho=0,t)$ is the peak intensity taking as axis z the axis of cavity 3, while w is the spot size radius of the laser beam, i.e. the radius for which the amplitude of the field is 1/e times that of the axis. Moreover, w is considered to be constant along axis z in cavity 3.

The following quantities are further defined:

$$P_s = \frac{\pi w^2}{2}I_s$$

$$G(t) \equiv \frac{I_0(t)}{I_s} = \frac{P(t)}{P_s}$$

At the gas pressure in cavity 3, preferably between 5 and 20 mbar, and in any case such that the Doppler and collisional widths are approximately equal (Voigt scheme), the intensity of saturation Is of transition P(20) is proportional to the collisional enlargement and to the relaxation rate of the population of the excited state, which is dominated by the exchange of energy with the other isotopologues of $CO_2$, therefore the absorption coefficient can be approximated by:

$$\alpha(t; \Delta v) = \frac{\alpha_0 g(\Delta v)}{1 + \frac{I(t)}{I_s}g(\Delta v)} \quad (6)$$

Where $\alpha_0$ is the absorption in laser-gas resonance non in saturation, $g(\Delta v)$ is a Voigt function normalized to 1 on the peak, $\Delta v$ is the deviation from the laser-gas resonance, I(t) is the intensity of the laser beam and Is the intensity of saturation. The integration of the curve of equation (6) on the Gaussian laser beam inside cavity 3 (see equation (5)) leads to the following decay:

$$\frac{dG}{dt} = -\gamma_c G - \gamma_g \ln(1 + G) \quad (7)$$

Where G is the saturation function:

$$G(t; \Delta v) = P(t)\frac{g(\Delta v)}{P_s} = P(t)U_s(\Delta v)$$

and $$P_s = \frac{\pi w^2}{2}I_s,$$

P(t) the power inside the cavity, $\gamma_g = c\alpha_0 g(\Delta v)$ and w is the spot size radius of the laser beam.

Therefore, γg is measured at each infrared frequency of the laser by a fit of the resulting decay curve.

An average of the various SCAR measures that are obtained at the same frequency is carried out so as to increase the signal/noise ratio of the spectrum.

Figure 4:
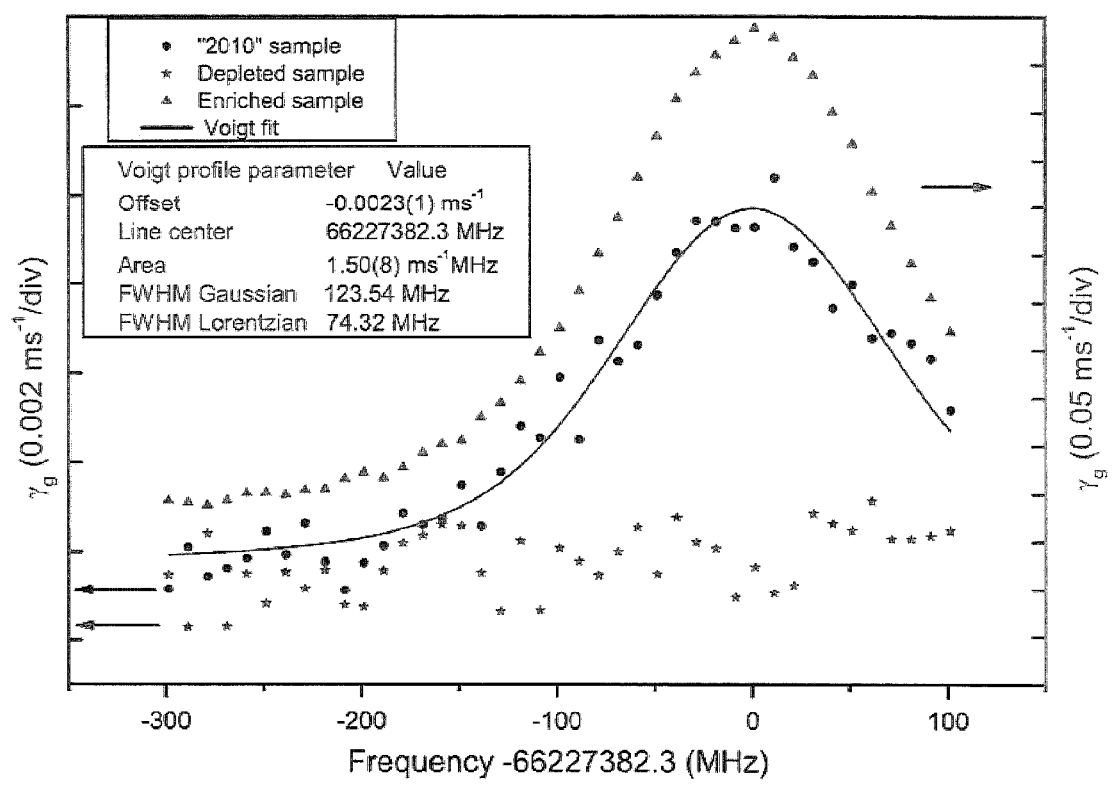
FIG. 4 is a spectrum of the roto-vibrational transition ($00^01$–$00^00$) P(20) of the molecule $^{14}C^{16}O_2$ in three different samples: sample in natural abundance (dots), sample enriched with carbon-14 (triangles), sample in which the carbon-14 has been removed (stars)

FIG. 4 shows the spectroscopy measurements carried out with apparatus 1 described above. Measurements were taken of a spectrum of a transition $^{14}C^{16}O_2$ P(20) in a sample in natural abundance, sample called "2010" in FIG. 4, as a recent sample on which there was no decay of carbon-14, these measurements are represented in FIG. 4 with dots. These measurements are compared to a sample enriched with carbon-14, graph in FIG. 4, with triangles, and a sample in which carbon-14 is substantially in traces shown in the graph with stars.

The spectrum obtained for the sample enriched in carbon-14 is useful for properly centering the desired transition P(20) as target. The measurement of the sample in natural abundance of carbon-14 leads, from the fit performed, to a concentration of 1.24(10) ppt which is in agreement with the measurements made in the literature.

Figure 5:
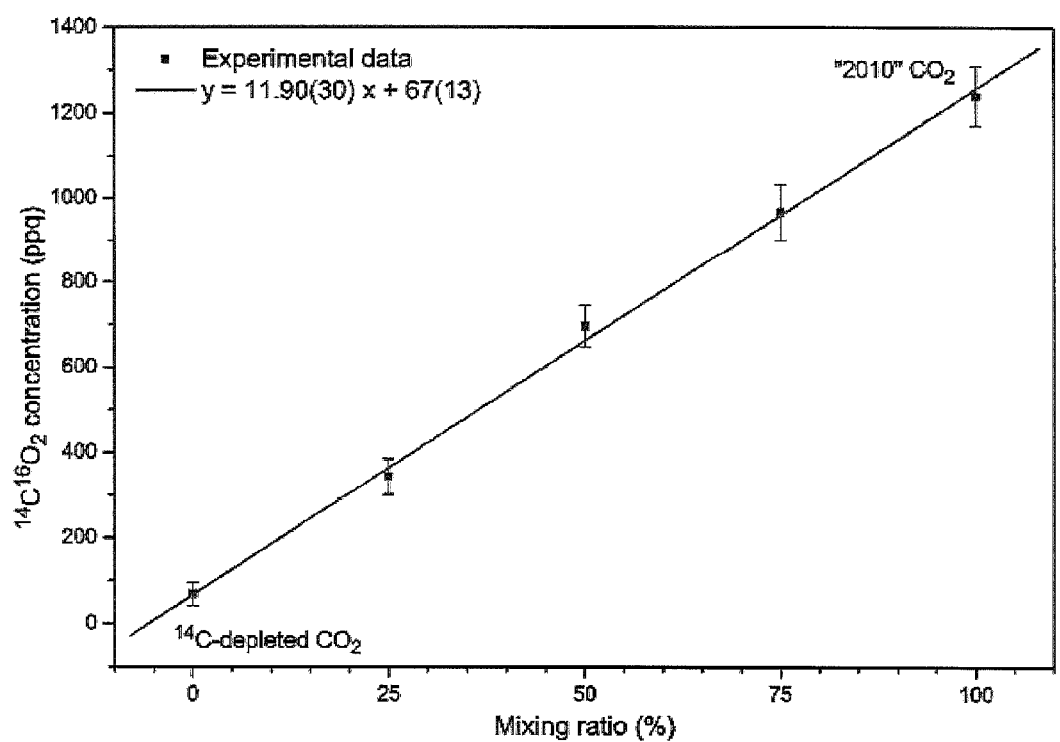
FIG. 5 is a graph that shows the linear pattern of the concentration of $^{14}C^{16}O_2$ measured against the dilution ratio of sample 2010 in natural abundance with a fossil sample with low radiocarbon content.

FIG. 5 is a graph that shows the linear pattern of the concentration of $^{14}C^{16}O_2$ measured against the dilution ratio of sample 2010 in natural abundance with a fossil sample with low radiocarbon content; The concentrations of $^{14}C^{16}O_2$ measured for sample 2010 and the fossil sample are represented by the two extreme points, at 100% and 0%, respectively, at a pressure of 11.6 mbar and at a temperature of 195 K. The samples for the intermediate points of the graph are obtained with a controlled mixing of sample 20'10 with the fossil sample, keeping the same total pressure and the same temperature.

Mixing the sample in natural abundance 2010 with that essentially free of carbon-14, the limit reached by the apparatus is also tested.

From this curve, the minimum concentration of carbon-14 that can be obtained which is equal to a density of $1.9\times10^4$ $cm^{-3}$ which corresponds to a pressure of $5\times10^{-16}$ bar can be estimate.

Figure 6:
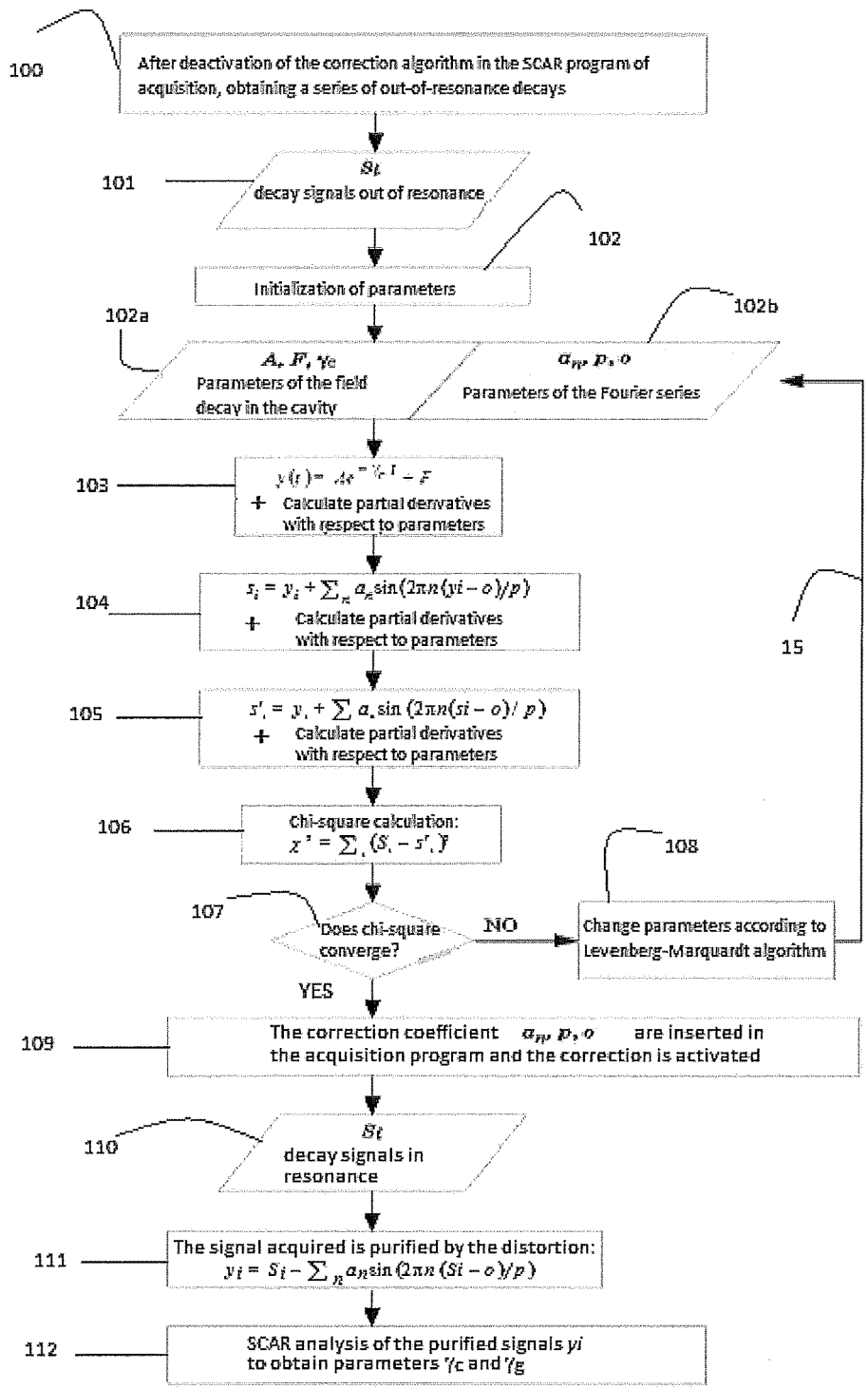
FIG. 6 is an exemplary flow diagram of the software linearization method of detection according to the invention.

The operating method of the apparatus is described hereafter with the aid of the diagram in FIG. 6.

In operation, a series of decays is first performed with the laser out of resonance of the species to be measured by acquiring various decay signals Si using the same or similar acquisition procedure as the measurements of the line profile of the spectrum, in as much as possible the same experimental conditions, step 100 and 101. These decay signals, after reaching photodetector 7, are acquired by processor 14 as such, i.e. without any interpolation.

The laser is brought out of resonance with the transition, for example by changing the wavelength of the electromagnetic radiation emitted by the same in a manner per se known in the field.

Subsequently, the algorithm of processor 14 provides to execute a fit of the decays.

The algorithm of processor 14 provides to initialize the value of the parameters to be used in the fit of decays, step 102.

The algorithm of processor 14 provides to initialize the value of the decay parameters of the radiation in cavity 3, i.e. A, F, γc of equation $\gamma(t)=Ae^{-\gamma_c t}+F$ that, as mentioned earlier, is assumed that describes the decay profile of the empty cavity, step 102a.

Subsequently, the algorithm of processor 14 provides to initialize the value of the parameters of the Fourier series an, p, o of expression $\Sigma_n a_n \sin(2\pi n(\gamma_i-o)/p)$, step 102b.

The partial derivatives are calculated with respect to the parameters of the two equations above, step 103, and subsequently the new function of the signal is calculated with the following equation: $s_i=y_i+\Sigma_n a_n \sin(2\pi n(yi-o)/p)$, step 104.

The algorithm of processor 14 preferably provides to recursively repeating the procedure, i.e. steps 103 and 104, one or more times, passing from $s_i$ to step 105.

Subsequently, the value of signal Si measured is compared with that calculated so as to determine for subsequent iterations the value of parameters A, F, γc, an, p, o which allow obtaining a convergence of the signal value measured and calculated. Preferably, the value of p is forced to be equal to 2A and or is fixed to the bottom value.

The value of the above parameters can be determined with a known fit procedure, for example with the ordinary method of minimization of the chi-square: $\chi^2 = \Sigma_i(s_i - s'_i)^2$, step 106.

The convergence of the chi-square is checked, step 107.

If the chi-square does not converge, the value of the parameters of the truncated Fourier series is changed, for example according to the Levenberg-Marquardt algorithm, step 108, and the procedure is repeated as indicated by arrow 15 in FIG. 6.

If the chi-square converges, the correction coefficients, i.e. the parameters of the truncated Fourier series are saved, i.e. included in the acquisition program, and the correction is applied to the signals to be detected, step 109, and then the actual acquisition is carried out, i.e. the decay signals are acquired in laser-gas resonance, step 110.

The values used for the parameters of the truncated Fourier series are stored in the acquisition algorithm to be used in subsequent measurements of the line profile. Therefore, the values obtained using a decay signal in laser-gas non-resonance are subsequently used in the measurement of the signal in laser-gas resonance from which the gas concentration is obtainable.

Subsequently, a detection is made of the decay signal in laser-gas resonance, the signal acquired by photodetector 7 is purified by the distortion using the equation:

$$y_i = S_i - \Sigma_n a_n \sin(2\pi n(Si-o)/p),$$

step 111.

Subsequently, the data of the single decay events that reach processor 14 from photodetector 7 are applied the SCAR interpolation process obtaining parameters γc and γg, step 112.

Figure 7A:
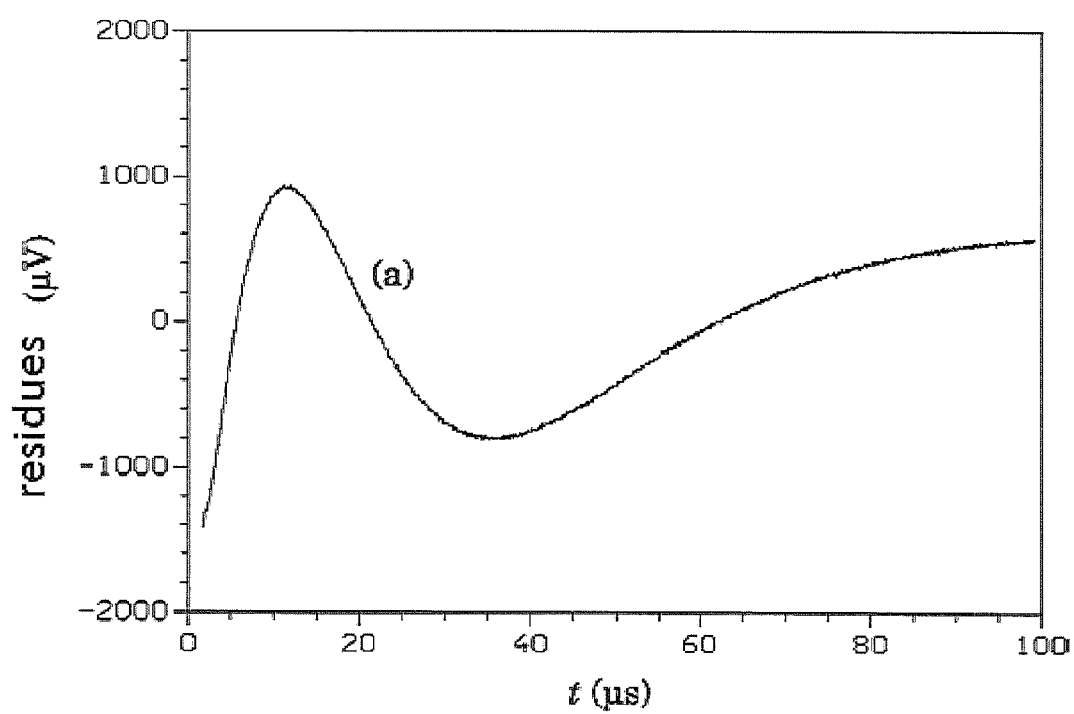
FIG. 7a is a graph showing the average of the residues of a fit with a simple exponential of 2 decay curves, each consisting of the average of 1280 decay signals, acquired with the electromagnetic radiation emitted by the laser out of resonance with the transition, with an apparatus of the prior art.
Figure 7B:
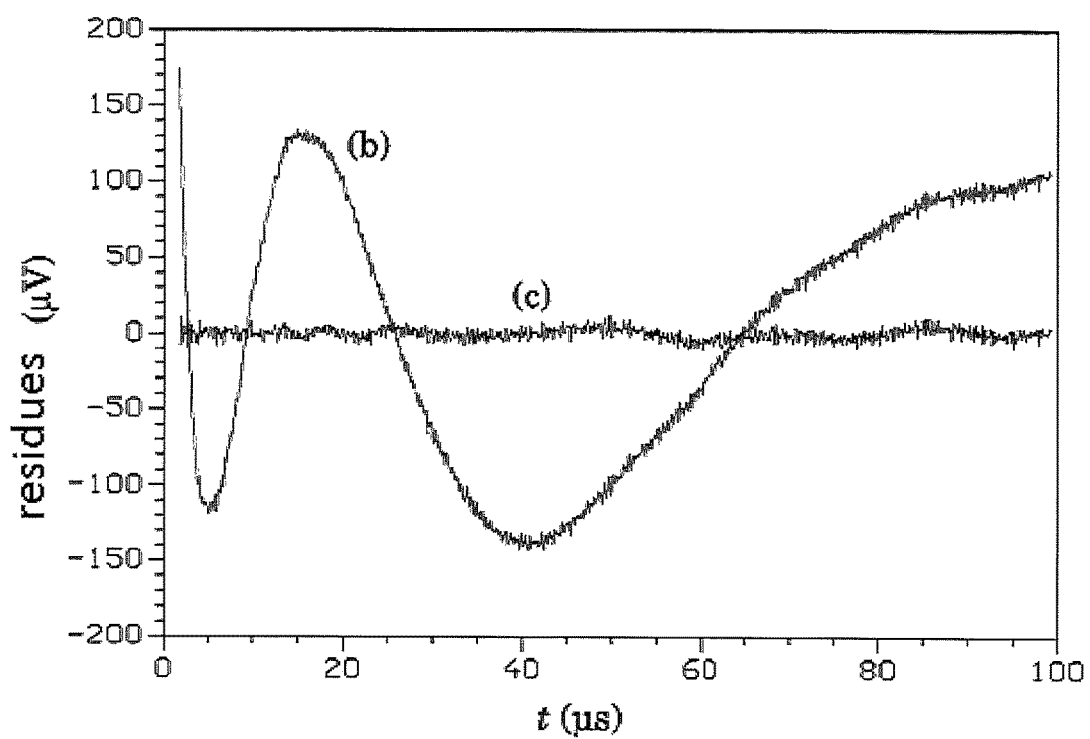
FIG. 7b is a graph showing the comparison between the residues of a fit with a simple exponential of the decay curves (each consisting of the average of 1280 decay signals) acquired with the electromagnetic radiation emitted by the laser out of resonance with the transition, with the apparatus in FIG. 2a as the average of the residues of 20 curves with diffuser and without software linearization, curve (b), and as the average of the residues of the same 20 curves after the software linearization procedure, curve (c).

The comparison between the graphs in FIGS. 7a and 7b allows graphically and quantitatively showing the advantages obtained in terms of reduction of the non-linearity of detection with the introduction of the surface diffuser 8a and with the use of the software linearization procedure.

FIGS. 7a and 7b show a comparison between the residues of a fit with a simple exponential of the decay curves (each consisting of the average of 1280 decay signals) acquired in laser-gas non-resonance.

The improvement demonstrated by a comparison between FIG. 7a, which shows the average of the residues of 2 curves without diffuser and without software linearization, and FIG. 7b curve (b), which shows the average of the residues of 20 curves with diffuser and without software linearization, is of about one order of magnitude.

The improvement shown by the comparison between curve (b) and curve (c) in FIG. 7b which shows the average of the residues of the same 20 curves after the software linearization procedure is over one order of magnitude.

Therefore, the overall improvement of the linearity of detection achievable with the apparatus of the invention is over 2 orders of magnitude.

Using a volumetric diffuser, for example as shown in FIG. 2b, a further improvement of the linearity of detection is obtained, approximately one order of magnitude, for the reasons highlighted above.

The use of diffuser 8 reduces the dependence on fluctuations due to the different optical alignments of the laser beam on cavity 3 and on photodetector 7, which would not be properly corrected with just the software method. In fact, even if the parameters of the correction software that linearize the response at a certain instant can be determined, these would no longer be valid in subsequent moments due to such fluctuations. Therefore, both correction methods of non-linearity are necessary.

The diffuser element 8, by preventing the signal from mainly reaching some points of photodetector 7 and reducing the spatial coherence of the beam on the illuminated surface of photodetector 7, by randomly varying the interference fringes that may form on the plane of the same, on a length scale smaller than that of the spatial heterogeneity of its response, allows increasing the uniformity of the signal that reaches photodetector 7.

In addition, the diffuser element 8, by decreasing the power of the signal that is focused on photodetector 7 itself, allows increasing the linearity of the signal.

The interpolation algorithm of processor 14 of the invention allows the other hand compensating for the non-linearity of the response of photodetector 7 and the conversion of the photocurrent in numbers that can be acquired by processor 14 (transimpedance preamplifier 12 and 18 bit digitizer 13).

Therefore, the precision obtainable with the apparatus of the invention is significantly improved compared to known devices.

The invention claimed is:

1. A ring-down spectrometry apparatus configured for saturated-absorption cavity ring-down spectroscopy and measuring a concentration of a gas through a measurement of a spectrum of a molecular transition of said gas, the apparatus comprising:

a tunable laser source adapted to emit an electromagnetic radiation beam having a predetermined wavelength in an infrared spectrum, the predetermined wavelength emitted by the tunable laser being selected and adjusted by a wavelength adjuster;

a resonant cavity adapted to contain said gas to be detected and comprising a first and a second reflecting mirror so as to form an optical path for the electromagnetic radiation emitted by said tunable laser source, a distance between said first and said second mirror being adjustable so as to couple said electromagnetic radiation to said cavity and bring said cavity in resonance or out of resonance with said electromagnetic radiation;

the wavelength adjuster configured to vary the wavelength of said radiation emitted by said tunable laser source so as to bring said electromagnetic radiation emitted by said laser in resonance or not in resonance with said molecular transition of said gas;

a photodetector adapted to detect an electromagnetic radiation beam in output from said cavity and adapted to generate a decay signal in laser-gas resonance or laser-gas non-resonance;

an electronic circuit configured to receive the signal in output from the photodetector and adapted to convert it in a signal in input to a processor;

a processor adapted to receive said decay signal from the photodetector, said processor:

adapted to perform an interpolation of said decay signal in laser-gas non-resonance so as to obtain one or more calibration coefficients as interpolation parameters;

adapted to subtract said calibration coefficients from the decay signal in laser-gas resonance so as to obtain a corrected decay signal in laser-gas resonance; and adapted to perform an interpolation of said corrected decay signal in laser-gas resonance so as to obtain a concentration of said gas as an interpolation parameter;

a diffuser element, disposed between said photodetector and said cavity, adapted to spread said electromagnetic radiation from said cavity on an optical plane of said photodetector.

2. The apparatus according to claim 1, wherein said first and said second mirrors have reflectivity greater than 99.9%.

3. The apparatus according to claim 1, wherein the processor is adapted to repeat said interpolation of said decay signal in laser-gas non-resonance and of said decay signal in laser-gas resonance at predetermined time intervals.

4. The apparatus according to claim 1, wherein the processor is adapted to average the corrected decay signal in laser-gas non-resonance N times.

5. The apparatus according claim 1, wherein a gas pressure inside said cavity is between 5 and 20 millibar (mbar), such that the Doppler and collisional widths are approximately equal so as to operate in Voigt condition.

6. The apparatus according to claim 1, wherein said diffuser element comprises a surface diffuser element.

7. The apparatus according to claim 1, wherein said diffuser element comprises a volume diffuser element.

8. The apparatus according to claim 1, wherein said diffuser element comprises a volume diffuser element combined with a surface diffuser element.

9. A method of saturated-absorption cavity ring-down spectroscopy, for measuring a concentration of a gas through a measurement of a spectrum of a molecular transition of said gas, comprising:

inserting said gas to be detected in a resonant cavity comprising a first and a second reflecting mirror arranged so as to form a closed optical path for an electromagnetic radiation emitted by a laser source;

irradiating said gas via an electromagnetic radiation beam emitted by said laser source having a predetermined wavelength and entered intermittently in said resonant cavity;

varying a distance between said first and second mirror so as to couple said electromagnetic radiation to said cavity so as to obtain a laser-cavity resonance condition;

determining an intensity of said light radiation in the cavity at a value greater than a saturation intensity of the molecular transition to be detected;

varying a wavelength of said electromagnetic radiation emitted by said laser source so that it is not in resonance with said molecular transition so as to obtain a laser-gas non-resonance;

detecting in laser-gas non-resonance an electromagnetic radiation beam in output from said cavity on an optical plane on which said radiation is diffused;

generating a live decay signal in laser-gas non-resonance on the basis of said detection;

interpolating said decay signal in laser-gas non-resonance so as to obtain a plurality of calibration coefficients of correction of a systematic error as an interpolation parameter;

adjusting a wavelength of said electromagnetic radiation emitted by said laser source so that it is in resonance with said molecular transition so as to obtain a laser-gas resonance;

diffusing said electromagnetic radiation coming from said cavity;

detecting in laser-gas resonance an electromagnetic radiation beam in output from said cavity on the optical plane on which said radiation is diffused;

generating a live decay signal in laser-gas resonance on the basis of said detection;

correcting said decay signal in laser-gas resonance with a function of said calibration coefficients calculated to generate a corrected decay signal;

interpolating said corrected decay signal in laser-gas resonance so as to obtain a concentration of said gas as the interpolation parameter.

10. Method according to claim 9, including: interpolating the deviation from an exponential of said decay signal in laser-gas non-resonance by a truncated Fourier series.

11. Method according to claim 9, including repeating said obtaining a plurality of calibration coefficients every predetermined time interval during the same ring-down measurement.

* * * * *